United States Patent [19]
Flood

[11] Patent Number: 6,121,446
[45] Date of Patent: Sep. 19, 2000

[54] PREPARATION OF TRIS-SUBSTITUTED ALKOXYCARBONYLAMINO-1,3,5-TRIAZINE COMPOUNDS

[75] Inventor: Lawrence Allen Flood, Norwalk, Conn.

[73] Assignee: Cytec Technology Corporation

[21] Appl. No.: 09/188,894

[22] Filed: Nov. 10, 1998

[51] Int. Cl.$^7$ .................................................. C07D 251/70
[52] U.S. Cl. .......................................... 544/196; 544/197
[58] Field of Search ..................................... 544/196, 197

[56] References Cited

U.S. PATENT DOCUMENTS

| | | | |
|---|---|---|---|
| 3,405,156 | 10/1968 | Stern et al. | 260/453 |
| 3,641,092 | 2/1972 | Henry et al. | 260/453 |
| 4,694,097 | 9/1987 | Alper et al. | 560/24 |
| 4,939,213 | 7/1990 | Jacobs, III et al. | 525/329.9 |
| 5,084,541 | 1/1992 | Jacobs, III et al. | 528/45 |
| 5,194,660 | 3/1993 | Leung et al. | 560/24 |
| 5,288,865 | 2/1994 | Gupta | 544/200 |
| 5,556,971 | 9/1996 | Bay et al. | 544/196 |
| 5,705,641 | 1/1998 | Flood et al. | 544/196 |
| 5,792,866 | 8/1998 | Flood et al. | 544/196 |

FOREIGN PATENT DOCUMENTS

| | | |
|---|---|---|
| 0 173 457 | 3/1986 | European Pat. Off. . |
| 0 200 556 | 11/1986 | European Pat. Off. . |
| 0 624 577 | 11/1994 | European Pat. Off. . |
| 0 649 842 | 4/1995 | European Pat. Off. . |
| WO96-11915 | 4/1996 | WIPO . |

OTHER PUBLICATIONS

E.M. Smolin et al., "S–Triazines and Derivatives," Interscience Publishers, Inc., New York, p. 333 (1959).

H. Alper et al., "An Exceptionally Mild, Catalytic Homogeneous Method for the Conversion of Amines into Carbamate Esters," *J. Chem. Soc., Chem. Commun.*, pp. 1141–1142 (1985).

S. Murahashi et al., "Palladium–catalysed Cross Double Carbonylation of Amines and Alcohols: Synthesis of Oxamates," *J. Chem. Soc., Chem. Commun.*, pp. 125–127 (1987).

Y. Tamaru et al., "Stereoselective Intramolecular Aminocarbonylation of 3–Hydroxypent–4–enylamides Catalyzed by Palladium," *Tetrahedron Letters*, vol. 265, No. 37, pp. 4479–4482 (1985).

P. Giannoccaro, "Palladium–catalysed N,N'–disubstituted urea synthesis by oxidative carbonylation of amines under CO and $O_2$ at atmospheric pressure," *Journal of Organometallic Chemistry*, vol. 336, pp. 271–278 (1987).

H. Alper et al., "Conversion of Primary Amines to Carbamate Esters Using Palladium Chloride and Di–tert–butyl Peroxide. Double Carbonylation of Secondary Amines," *Organometallics*, vol. 6, pp. 2391–2393 (1987).

V.A. Golodov et al., "Oxidative Carbonylation Catalyzed by Transition Metal Complexes", *Fundam. Res. Homog. Catal.*, 3, pp. 239–256 (1979).

*Primary Examiner*—John M. Ford
*Attorney, Agent, or Firm*—Pennie & Edmonds LLP

[57] ABSTRACT

The present invention relates to a method for preparing tris-substituted alkoxycarbonylamino-1,3,5-triazine compounds, which involves reacting a amino-1,3,5-triazine compound such as melamine, for example, in the presence of excess amounts of carbon monoxide and an alcohol, a sub-stoichiometric amount of a base, a catalyst system that includes a catalytic amount of a primary catalyst of a group VIII metal or metal salt, and a sub-stoichiometric amount of a co-catalyst of a group I-B or lanthanide series metal or metal salt. The reaction is conducted at a temperature, pressure and length of time sufficient to form a tris-substituted alkoxycarbonylamino-1,3,5-triazine compound in a yield of at least about 5 percent, with improved yields of more than 40 percent being conveniently obtained.

32 Claims, No Drawings

PREPARATION OF TRIS-SUBSTITUTED ALKOXYCARBONYLAMINO-1,3,5-TRIAZINE COMPOUNDS

TECHNICAL FIELD

This application relates to an improved carbonylation process for the production of tris-substituted alkoxycarbonylamino-1,3,5-triazine compounds.

BACKGROUND OF THE INVENTION

Carbamate esters, also known as urethanes, have a variety of uses, such as in the production of polyurethanes, isocyanates, and pesticides. These esters are generally prepared by: (1) reacting with an amine a chloroformate ester that is obtained by reacting phosgene with an alcohol; or (2) by reacting an isocyanate with an alcohol. U.S. Pat. No. 5,556,971 discloses a process for preparing isocyanate and isocyanate-based 1,3,5-triazine derivatives by the direct phosphogenation of an at least tris-unsubstituted amino-1,3,5-triazine. PCT publication WO 96/11915 discloses a process for preparing acid amides, including isocyanate-functional 1,3,5-triazines and isocyanate-based 1,3,5-triazine derivatives, from the reaction of silicon, germanium or tin substituted amino-1,3,5-triazines and acid halides. Both phosgene and isocyanates are considered as undesirable reactants due to their toxicity.

Many derivatives of amino-1,3,5-triazines are utilized in a wide variety of applications, as described in the literature. One important use of certain of these derivatives, such as methoxymethyl derivatives of melamine and guanamines, is as crosslinkers in curable compositions. Although these triazine derivatives are useful for such applications, formaldehyde may be undesirably released as a volatile by-product during curing. As a result, there is much interest in finding alternative 1,3,5-triazine derivatives that do not emit formaldehyde upon curing.

One such alternative are the alkoxycarbonylamino-1,3,5-triazines, also known as triazine carbamate esters. U.S. Pat. No. 5,288,865 discloses a one step process for the preparation of carbamate functional 1,3,5-triazines by reacting a haloamino-1,3,5-triazine with an acid halide.

U.S. Pat. Nos. 4,939,213 and 5,084,541 each disclose a process for preparing 1,3,5-triazine carbamates in two steps. Both steps involve reacting an amino-1,3,5-triazine with oxalyl chloride to produce an isocyanate intermediate, then further reacting the intermediate with an alcohol. The resulting 1,3,5-triazine carbamates are potentially useful crosslinkers in coating compositions that are based upon hydroxy functional resins. There are disadvantages to this process, including the required use of certain costly halogenated starting materials, the production of significant amounts of halogenated by-products, and the low overall yield of the desired products.

Replacing oxalyl chloride with carbon monoxide in the carbonylation step solves the problems associated with halogenated reactants and products. Thus, U.S. Pat. Nos. 3,405,156 and 3,641,092 disclose processes for carbonylation of amines in the presence of a catalyst to form isocyanates. It is generally known that carbamates may be formed by subsequent reaction of isocyanates with an alcohol to produce the corresponding carbamate ester, and this was further shown in both cases.

U.S. Pat. No. 4,694,097 discloses a process for producing carbamate esters by reacting an amine with carbon monoxide and an alcohol in the presence of a protonic acid, a dehydrating agent, and a catalyst. The protonic acid and the dehydrating agent are reported to be key components in this process.

Similarly, European Patent Application No. 173,457 discloses a process for producing aromatic carbamate esters from aromatic amines, carbon monoxide, an alcohol, and a protonic acid in the presence of a catalyst.

U.S. Pat. No. 5,194,660 discloses a process for producing carbamates by reacting primary amines, secondary amines, and/or ureas with carbon monoxide, an organic hydroxyl compound, an oxidizing agent, a halide, and a catalytic metal macrocyclic complex.

European Patent Application No. 649,842 discloses a process for producing carbamates by the carbonylation of triazines. The process involves the reaction of a triazine with carbon monoxide and an alcohol in the presence of a metal catalyst system and an oxidant system. In the specific case of reacting a tris-amino-1,3,5-triazine, mono- and bis-carbamate triazines were formed, but small amounts (e.g., less than 6%) of the tris-carbamate triazine was formed.

European Patent Application No. 624,577 and U.S. Pat. Nos. 5,705,641 and 5,792,866 disclose a process for producing bis-carbamate functional 1,3,5-triazines by reacting diamino-1,3,5-triazines with an acyclic organic carbonate and a base. Yields of between 30 to 80% tris-carbamate triazines were reportedly obtained.

It is also generally known that carbamates may be obtained via the carbonylation of amines in the presence of an alcohol. However, as it is well known to the skilled person in the art that the amine functionality of amino 1,3,5-triazines (such as amine functionalities of melamines and guanamines) is not equivalent to the other types of typical amine functionality, one of ordinary skill in the art would not reasonably expect success when conducting multiple carbonylations on tris-amino-1,3,5-triazines.

Furthermore, melamines and guanamines are among the least reactive of the amines and, thus, the most difficult to functionalize. Their behavior is not normally correlated to that of other known amines, even structurally similar amines such as pyrimidines. For example, most typical amines are highly reactive with acyl halides. Smolin el al. reported unsuccessful attempts to acylate all three amino groups of melamine (E. M. Smolin and L. Rappaport, "S-Triazines and Derivatives", Interscience Publishers Inc., New York, 1959, pg 333).

There is thus a need for a process for producing tris-carbamates that can function as environmentally friendly crosslinkers by not emitting formaldehyde upon curing. To date, no process of efficiently producing tris-carbamates by carbon monoxide have been reported. The present invention now satisfies this need.

SUMMARY OF THE INVENTION

This invention relates to a process for preparing tris-alkoxycarbonylamino- 1,3,5-triazine compounds by reacting a tris-(halo)amino triazine compound with excess amounts of carbon monoxide and an alcohol, a sub-stoichiometric amount of a base, and a catalyst system comprising a catalytic amount of a primary catalyst of a group VIII metal or metal salt and a sub-stoichiometric amount of a co-catalyst of a group I-B or lanthanide series metal or metal salt. Suitable reaction conditions, with consideration to temperature, pressure and length of time, are utilized to form tris-alkoxycarbonylamino-1,3,5-triazine compounds in a yield of at least about 5 percent. In a preferred embodiment, a yield of at least 10 percent was achieved. In more preferred embodiments, yields of 25 to 40 percent or more were easily achieved.

The triazine compounds suitable for use in the present invention are (halo)amino-1,3,5-triazine compounds, which are represented by the formula:

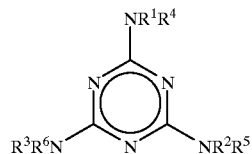

wherein $R^1$, $R^2$, and $R^3$ are the same or different and each is hydrogen, halogen, hydroxy, hydrocarbyl and hydrocarbyloxy hydrocarbyl, nitroso, sulfanyl, aralkyl, or aryl whereby $R^1$, $R^2$, and $R^3$ are substituted or unsubstituted; and $R^4$, $R^5$, and $R^6$ are the same or different and each is hydrogen or halogen. The typical (halo)amino-1,3,5-triazine is one where $R^1$, $R^2$, and $R^3$ are each independently hydrogen, halogen, $C^1$ to $C^6$ alkyl, $C^3$ to $C^8$ cycloalkyl, $C^2$ to $C^6$ alkenyl, $C^2$ to $C^6$ alkynyl, and $C^1$ to $C^6$ alkoxy; and $R^4$, $R^5$, and $R^6$ are hydrogen or halogen. The preferred (halo)amino-1,3,5-triazine is melamine, where $R^1$, $R^2$, $R^3$, $R^4$, $R^5$, and $R^6$ are each a hydrogen atom.

The reaction is preferably carried out under a pressure of about 250 psig to 1500 psig, and at temperatures of about 40° C. to 150° C. Suitable alcohols are monohydric or polyhydric alkanols, alkenols, cycloalkanols and arylalkanols.

Advantageously, the primary catalyst is derived from a group VIII metal, such as palladium, platinum, ruthenium, rhodium, or a mixture thereof. To regenerate the primary catalyst in-situ, an oxidant system may be used, such as one which includes a molecular oxygen-containing gas and a lanthanide or a group I-B metal. In addition, the lanthanide or group I-B metal can also act as a co-catalyst.

The base that is used in the reaction is preferably one that has a $pK_a$ of about 4 to about 13. In another embodiment, the reaction may be conducted in the presence of a solvent, preferably of an alkyl nitrile, aryl nitrile, or a mixture thereof.

DETAILED DESCRIPTION OF THE PREFERRED EMBODIMENTS

The present invention discloses an improved carbonylation process for the production of tris-substituted alkoxycarbonylamino-1,3,5-triazine compounds, having a higher yield than previously found in such processes. This process includes the step of reacting a (halo)amino-1,3,5-triazine compound with excess carbon monoxide and an alcohol, a sub-stoichiometric amount of a base, and a catalyst system under suitable conditions to produce a tris-alkoxycarbonylamino-1,3,5-triazine compound. The catalyst system includes a primary catalyst of a group VIII metal or metal salt, and a sub-stoichiometric amount of a co-catalyst of a group I-B metal or lanthanide series metal or metal salt. The term "sub-stoichiometric" is defined as the amount of a reactant used in a reaction that is more than catalytic but less than stoichiometric. The terms "tris-alkoxycarbonylamino-1,3,5-triazine" and "tris-carbamate ester" are used interchangeably in the context of the present invention. The term "(halo)" within the term tris-(halo) amino triazine, is used to denote either halo or non-halo substituted compounds.

The advantages of the present process include, for example:

i. the present process can effectively carbonylate all three amino groups of a tris-(halo)amino-1,3,5-triazine compound;

ii. the present process does not require the use of an acid;

iii. the present process does not require the use of costly halogenated reagents, such as oxalyl chloride;

iv. the present process does not require the handling or isolation of an isocyanate intermediate.

It has been surprisingly discovered that tris-carbamate esters derived from tris-(halo)amino triazines can be readily synthesized with high selectivity and yield using the present inventive process. Under suitable reaction conditions, tris-carbamate esters can be formed in typical yields of as high as 40 to 80 percent.

The components are preferably reacted at temperatures between about 40° C. to about 150° C., more preferably between about 70° C. to about 100° C., and most preferably between about 75° C. to 85° C. At these temperatures, and depending on the starting components, nearly complete conversion was found to occur between about 2 hours and 24 hours. The components can be reacted either by a batch or continuous flow system. Preferably, the reaction is done in a batch reactor, such as an autoclave.

The term "hydrocarbyl" in the context of the invention is defined as a group which contains exclusively carbon and hydrogen atoms and includes, for example, alkyl, aryl, aralkyl, alkenyl, and substituted derivatives thereof.

The carbon monoxide that can be employed in the present invention may be pure carbon monoxide or may contain other gases or "impurities", such as, for example, nitrogen, argon, helium, carbon dioxide, oxygen, air, a hydrocarbon, or a halogenated hydrocarbon. Generally, any commercially available carbon monoxide may be utilized. It is preferred, however, that the carbon monoxide be substantially free of water. Preferred carbon monoxide pressures are between about 120 psig to 1500 psig. More preferably, the carbon monoxide pressure is approximately about 650 psig to 1050 psig. Most preferably, the carbon monoxide pressure is about 700 psig to 850 psig.

Any metal catalyst system containing a metal capable of facilitating carbonylation of the (halo)amino groups of 1,3,5-triazine is suitable for the process of the present invention. Preferably, the metal catalyst is a group VIII metal or a compound containing a group VIII metal, including mixtures or complexes thereof. More preferably, the metal catalyst includes palladium, platinum, ruthenium, rhodium, or mixtures or compounds thereof, and especially the oxides, halides and organic salts of these metals. The most preferred metal catalysts are palladium (0), and palladium compounds including palladium chloride, palladium bromide, palladium iodide, palladium (II) bis-acetonitrile dichloride, palladium acetate, palladium acetylacetonate, palladium oxide, or mixtures thereof. Various metal catalysts, such as palladium (0) and palladium (II) salts, may be used on a variety of supports, for example, alumina, silica, barium sulfate, calcium carbonate, aluminosilicates, zeolites, clays, carbonaceous material, intercalated material, resins and other polymeric materials.

The term "mole percent" is used herein relative to the moles of amino groups present in the reaction. Preferably, the primary catalyst is present in the reaction in an amount from about 0.05 mole percent to 20 mole percent. More preferably, the primary catalyst is present in the reaction in an amount from about 0.1 mole percent to 2 mole percent.

Relatively large amounts of metal catalyst are required to facilitate the carbonylation of amino groups to isocyanates or carbamate functional 1,3,5-triazines in high yields. It is believed that the metal catalyst is reduced under carbonylation conditions, rendering it catalytically inactive. Thus, it is preferred to utilize an oxidant system with the metal catalyst during the carbonylation, as this will significantly reduce the amount of metal catalyst required to produce desirable high yields of tris compounds to normal catalytic levels i.e. less than about 20 mole percent based on amino groups.

Any oxidant system capable of restoring the metal catalyst to an effective oxidation state is suitable in the present invention as the oxidant system. The oxidant system typically includes an ingredient or a plurality of ingredients capable of accepting one or more electrons from the reduced metal catalyst, and thereby restoring the metal catalyst to an oxidation state that is suitable to carry out another carbonylation reaction. The term "regeneration", in the context of the invention, refers to the process of restoring the metal catalyst to an effective oxidation state suitable to carry out a carbonylation reaction.

The oxidant system effectively regenerates the metal oxidation state, enabling the regenerated species to facilitate the carbonylation reaction through a multiplicity of cycles. The term "turn over numbers" or "TON" in the context of the invention, refers to the number of cycles a metal catalyst is involved in during the course of a reaction. Preferred oxidant systems include molecular oxygen, any oxygen-containing gas, a metal, a metal-containing compound, or any mixtures thereof. More preferably the oxidant system includes a group I-B metal or lanthanide and an oxygen-containing gas, which includes, for example, air and oxygen, wherein about 1 to 20 mole percent group I-B metal or lanthanide and from about 50–500 psig air are present. Most preferably, the oxidant system includes copper(II) chloride and air, wherein about 5 mole percent to 10 mole percent copper(II) chloride and at least a stoichiometric amount of air is present. An advantage is that only a catalytic amount of the group I-B metal or lanthanide is sufficient to carry out the reaction, in contrast to the higher stoichiometric amounts required in prior art-carbonylation processes. The Group I-B metal and lanthanide metal described in the oxidant system may have other specific functions, and functions as a co-catalyst.

Carbamate functional 1,3,5-triazine compounds may be readily produced in accordance with the present inventive process by one of two routes:

1. reacting a amino-1,3,5-triazine compound, carbon monoxide and the above-described components in the presence of an alcohol, or
2. post-reacting the intermediate, for example isocyanate, 1,3,5-triazine compound with an alcohol.

A wide variety of alcohols are suitable for use in forming carbamate functional 1,3,5-triazine compounds. Suitable alcohols are branched and straight chain monohydric and polyhydric alkanols, branched or straight chained monohydric or polyhydric alkenols, monohydric or polyhydric cycloalkanols, monohydric or polyhydric arylalcohols, or a mixture thereof. More preferably, the alcohol is a straight or branched monohydric or polyhydric alkanol of about 1 to 20 carbon atoms. Examples of more preferred alcohols include methanol, ethanol, 1-propanol, isopropanol, 1-butanol, 2-butanol, isobutanol, tertiary butyl alcohol, 1-pentanol, 2-pentanol, 3-pentanol, isopentanol, 3-methyl-2-butanol, 2-methyl-2-butanol, 2-methyl-1-pentanol, neopentanol, 1-hexanol, 2-hexanol, 3-hexanol, 2-methyl-1-pentanol, 2-methyl-2-pentanol, 2-methyl-3-pentanol, 4-methyl-2pentanol, 4-methyl-1-pentanol, 3-methyl-1-pentanol, 3-methyl-2-pentanol, 3-methyl-3-pentanol, 3-methylol pentane, neohexylalcohol, 3,3-dimethyl-2-butanol, 2,2-dimethyl-1-butanol, 2,3-dimethyl-1-butanol, 2,3-dimethyl-2-butanol, cyclopropanol, cyclobutanol, cyclopentanol, cyclohexanol, heptanol, octanol, benzyl alcohol, phenol, allyl alcohol, ethylene glycol, propylene glycol, 1,3-propanediol, 1,4-butanediol, 1,3-butanediol, ethoxyethanol, hydroxyethoxyethanol, 1-methoxy-2-propanol, 1-heptanol, 1-octanol, or a mixture thereof. Most preferably, the alcohol is 1-butanol, methanol, or a mixture thereof. Mixtures of 1-butanol to methanol may range from about 10:1 to 1:10. Furthermore, these alcohols may have a substituent such as a halogen atom, a sulfoxide group, a carbonyl group, an ether group, an ester group, an amide group, a cyano group, an alkoxy group, a nitro group or mixtures thereof.

The process herein may be conducted in the absence of a co-solvent since the alcohol functions as a reactant but also serves its purpose as a solvent. For this reason, the alcohol is typically present in large excess compared to the (halo) amino-1,3,5-triazine compound, with alcohol to (halo) amino-1,3,5-triazine compound ratios of up to about 200 to 1. A large excess is particularly preferred when no co-solvent is used.

In another embodiment, a co-solvent is present in the process, wherein the co-solvent is a nitrile solvent. Preferably, the nitrile solvent is an alkyl nitrile, aryl nitrile, or a mixture thereof. More preferably, the nitrile solvent is acetonitrile, propyl nitrile, butyl nitrile, benzonitrile, benzyl nitrile, and mixtures thereof. Most preferably, the nitrile solvent is acetonitrile. 1-Butanol/acetonitrile mixtures may be used, ranging from a ratio of butanol to acetonitrile of about 1:1 to 100:1.

A base is also present in the inventive process. Without being bound to any theory, the base is believed to enhance the catalytic ability of the catalyst system. Preferably, the base is a weak organic or inorganic base. More preferably, the base has a $pK_a$ in the range of about 4 to 13. Examples of suitable bases include sodium phosphate, sodium phosphate dibasic, sodium pyrophosphate, potassium phosphate dibasic, lithium phosphate, sodium acetate, or ammonium phosphate dibasic, present in a base/metal oxidant ratio from about 1:4 to 4:1, wherein the metal oxidant is preferably copper dichloride. Preferably, the base is sodium phosphate, dibasic or sodium phosphate in a base/metal oxidant ratio of about 2:1 to 1:2. More preferably, the base is sodium phosphate dibasic in a sodium phosphate dibasic/copper dichloride ratio of about 1:1.

It is preferred to conduct the carbonylation process in the absence of water. The presence of water may cause side reactions, such as the hydrolysis of isocyanates and carbamates, and the water gas reaction of carbon monoxide. In another embodiment, the carbonylation process may be conducted in the presence of a molecular sieve, for example 3A, 4A, and 5A.

EXAMPLES

The invention is further defined by reference to the following examples describing in detail the preparation of the compounds and the compositions used in the methods of the present invention, as well as their utility. The examples are representative and should not be construed to limit the scope of the invention.

Example 1

Carbonylation of Melamine in the Presence of 1-Butanol with a $PdCl_2/CuCl_2$ Catalyst System Melamine was contacted with carbon monoxide at about 69 bar gauge (1000 psig) and at ca. 80° C. for 24 hours in 1-butanol. A quantity of oxygen in 20% excess over stoichiometric (based on amino groups) was present. A catalytic quantity of Pd(II)Cl$_2$ (at 1 mol % Pd based on amino groups) was used with Cu(II)Cl$_2$ as co-catalyst (at 10 mol % Cu based on amino groups)

A glass-lined, two liter, 316 stainless steel ZIPPER-CLAVE® was charged with the following:

melamine (7.58 g, 60 mmol)

sodium phosphate, dibasic (Na$_2$HPO$_4$) (2.57 g, 17.9 mmol)

copper(II) chloride, CuCl$_2$, (2.42 g, 18.0 mmol)

palladium(II) chloride, PdCl$_2$, (0.3212 g, 1.81 mmol) and 1-butanol (600 mL).

The reactor and reaction mixture were purged with nitrogen. The reactor was pressurized to about 34.5 bar gauge (500 psig) with carbon monoxide at room temperature. Air was charged to the reactor to a total pressure of about 43.5 bar gauge (630 psig). The reaction temperature was brought to ca. 80° C., and the system was furthered pressurized to about 69 bar gauge (1000 psig) with carbon monoxide. The reaction mixture was stirred under these conditions for approximately 24 hours. The reactor was cooled to room temperature, and the carbon monoxide pressure vented. Nitrogen purge cycles were used to remove dissolved carbon monoxide from the reaction mixture.

Approximately half of the product (197.51 g) was charged to a filtration funnel containing CELITE® covered with a layer of silica gel. The dried product (10.22 g) containing the N-butoxycarbonylamino-1,3,5-triazines, was obtained by removing 1-butanol from the filtrate under reduced pressure. A catalytic turnover number (TON) of 83 (mole butoxycarbonylamino groups/mole palladium) was determined from $^1$H-NMR. Product composition and total overall yield as determined by $^1$H-NMR was as follows: Tris-2,4,6-butoxycarbonylamino-1,3,5-triazine, 78%; Bis-(2,4-butoxycarbonylamino)-6-amino-1,3,5-triazine, 12%; mono-2-butoxycarbonylamino-4,6-diamino-1,3,5-triazine, 3%.

Example 2

Carbonylation of Melamine in the Presence of 1-Butanol with a Pd(0)/CuCl$_2$ Catalyst System The process of Example 1 was repeated except that a catalytic quantity of Pd(0) (at 1 mol % Pd based on amino groups) was used.

A glass-lined, two liter, 316 stainless steel ZIPPER-CLAVE® was charged with the following:

melamine (7.57 g, 60 mmol)

sodium phosphate, dibasic (Na$_2$HPO$_4$) (2.56 g, 17.9 mmol)

copper(II) chloride, CuCl$_2$, (2.41 g, 18.0 mmol)

palladium(0) metal, Pd(0), (3N5 powder, 60 mesh; 0.1909 g, 1.79 mmol) and 1-butanol (600 mL).

The reaction was conducted as disclosed in Example 1. Approximately half of the product (197.16 g) was charged to a filtration funnel containing CELITE® covered with a layer of silica gel. The dried product (6.35 g) containing the N-butoxycarbonylamino-1,3,5-triazines, was obtained by removing 1-butanol from the filtrate under reduced pressure. A catalytic turnover number (TON) of 60 (moles butoxycarbonylamino groups/mole palladium) was determined from $^1$H-NMR. Product composition and total overall yield as determined by $^1$H-NMR was as follows: Tris-2,4,6-butoxycarbonylamino-1,3,5-triazine, 56%; Bis-(2,4-butoxycarbonylamino)-6-amino-1,3,5-triazine, 5%; mono-2-butoxycarbonylamino-4,6-diamino-1,3,5-triazine, 1%.

Comparative Example A

Carbonylation of Melamine in the Presence of 1-Butanol with Pd(0) Catalyst System Example 2 of European Patent Application 649,842 discloses a similar process except no cocatalyst is used, the base is sodium iodide, and the reaction temperature is 170° C. Further analysis of the product composition and total overall yield as determined by $^1$H NMR was as follows: Tris-2,4,6-butoxycarbonylamino-1,3,5-triazine 0%, Bis-(2,4-butoxycarbonyl-amino-1,3,5-triazine 2%, mono-2-butoxycarbonylamino-4,6-diamino-1,3,5-triazine 18%. The lack of formation of the Tris product is believed to be due to the absence of the cocatalyst.

Comparative Example B

Carbonylation of Melamine in the Presence of 1-Butanol with Cu(0) Catalyst System Example 15 of European Patent Application 649,842 discloses a similar process except Cu(0) (powder, 150 mesh) is used, the base is potassium iodide, and the reaction temperature is 150° C. Further analysis of the product composition and total overall yield as determined by $^1$H NMR was as follows: Tris-2,4,6-butoxycarbonyl-amino-1,3,5-triazine 0%, Bis-(2,4-butoxycarbonyl-amino-1,3,5-triazine 0.6%, mono-2-butoxycarbonylamino-4,6-diamino-1,3,5-triazine 8%. The lack of formation of the Tris product is believed to be due the absence of the cocatalyst.

Example 3

Carbonylation of Melamine in the Presence of 1-Butanol with a Pd(OAc)$_2$/CuCl$_2$ Catalyst System The process of Example 1 was repeated except that a catalytic quantity of Pd(OAc)$_2$ (at 1 mol % Pd based on amino groups) was used.

A glass-lined, two-liter, 316 stainless steel ZIPPER-CLAVE® was charged with the following:

melamine (7.58 g, 60 mmol)

sodium phosphate, dibasic (Na$_2$HPO$_4$) (2.57 g, 18.1 mmol)

copper(II) chloride, CuCl$_2$, (2.42 g, 18.0 mmol)

palladium(II) acetate, Pd(OAc)$_2$, (0.4043 g, 1.80 mmol) and anhydrous 1-butanol (600 mL).

The reaction was conducted as in Example 1 except the reaction was carried out for 4 hours and the reaction vessel was initially pressurized to 52 bar gauge (750 psig) before air (130 psig) was added. The reaction was heated to ca. 80° C., which gave a final total pressure of 69 bar gauge (1000 psig).

Approximately 94% of the product mixture (458.48 g) was charged to a medium-fritted filtration funnel. The dried product (11.23 g) containing the N-butoxycarbonylamino-1,3,5-triazines, was obtained by removing 1-butanol from the filtrate under reduced pressure. A catalytic turnover number (TON) of 44 (mole butoxy-carbonylamino groups/mole palladium) was determined from $^1$H-NMR. Product composition and total overall yield as determined by $^1$H-NMR was as follows: Tris-2,4,6-butoxycarbonylamino-1,3,5-triazine, 42%, Bis-(2,4-butoxycarbonylamino)-6-amino-1,3,5-triazine 3%, mono-2-butoxycarbonylamino-4,6-diamino-1,3,5-triazine 0%.

Example 4

Carbonylation of Melamine in the Presence of 1-Butanol with a Pd(AcAc)$_2$/CuCl$_2$ Catalyst System The process of Example 1 was repeated except a catalytic quantity of Pd(AcAc)$_2$ (at 1 mol % Pd based on amino groups) was used.

A glass-lined, two-liter, 316 stainless steel ZIPPER-CLAVE® was charged with the following:

melamine (7.57 g, 60 mmol)

sodium phosphate, dibasic ($Na_2HPO_4$) (2.56 g, 18.0 mmol)

copper(II) chloride, $CuCl_2$, (2.42 g, 18.0 mmol) palladium (II) acetylacetonate, $Pd(AcAc)_2$, (0.5374 g, 1.76 mmol) and anhydrous 1-butanol (600 mL).

The reaction was conducted as in Example 1 except the reaction was carried out for 4 hours and the reaction vessel was initially pressurized to 52 bar gauge (750 psig) before air (130 psig) was added. The reaction was heated to ca. 80° C., which gave a final total pressure of 69 bar gauge (1000 psig).

Approximately 96% of the product mixture (452.05 g) was charged to a medium-fritted filtration funnel. The dried product (12.25 g) containing the N-butoxycarbonylamino-1,3,5-triazines, was obtained by removing 1-butanol from the filtrate under reduced pressure. A catalytic turnover number (TON) of 48 (mole butoxy-carbonylamino groups/mole palladium) was determined from $^1$H-NMR. Product composition and total overall yield as determined by $^1$H-NMR was as follows: Tris-2,4,6-butoxycarbonylamino-1,3,5-triazine 44%, Bis-(2,4-butoxycarbonylamino)-6-amino-1,3,5-triazine 5%, mono-2-butoxycarbonylamino-4,6-diamino-1,3,5-triazine 0%.

Example 5

Carbonylation of Melamine in the Presence of a Mixed Solvent System (1-Butanol/Methanol) with the $PdCl_2$/$CuCl_2$ Catalyst System The process of Example 1 was repeated except that a 5:1 butanol/methanol mixture was used.

A glass-lined, two-liter, 316 stainless steel ZIPPER-CLAVE® was charged with the following:

melamine (7.57 g, 60 mmol)

sodium phosphate, dibasic ($Na_2HPO_4$) (2.53 g, 17.8 mmol)

copper(II) chloride, $CuCl_2$, (2.42 g, 18.0 mmol)

palladium(II) chloride, $PdCl_2$, (0.3214 g, 1.81 mmol)

1-butanol, (490 mL) and methanol (110 mL).

The reaction was conducted as disclosed in Example 1. Approximately one-half of the product (206.13 g) was charged to a filtration funnel containing CELITE® covered with a layer of silica gel. The dried product (12.21 m g) containing the N-butoxycarbonylamino-1,3,5-triazines, was obtained by removing 1-butanol and methanol from the filtrate under reduced pressure. A catalytic turnover number (TON) of 86 (mole (butoxy, methoxy)-carbonylamino groups/mole palladium) was determined from $^1$H-NMR. Product composition and total overall yield as determined by $^1$H-NMR was as follows: Tris-2,4,6-(butoxy, methoxy) carbonylamino-1,3,5-triazines 79%, Bis-(2,4-(butoxy, methoxy)carbonylamino)-6-amino-1,3,5-triazines 12%, mono-2-butoxycarbonylamino-4,6-diamino-1,3,5-triazine and mono-2-methoxy-carbonylamino-4,6-diamino-1,3,5-triazines 0.8%.

Example 6

Carbonylation of Melamine in the Presence of a Mixed Solvent System (1-Butanol/Acetonitrile) with a $PdCl_2$/$CuCl_2$ Catalyst System The process of Example 1 was repeated except that a 5:1 butanol/acetonitrile solvent mixture was used.

A glass-lined, two-liter, 316 stainless steel ZIPPERCLAVE® was charged with the following:

melamine (7.57 g, 60 mmol)

sodium phosphate, dibasic ($Na_2HPO_4$) (2.56 g, 18.0 mmol)

copper(II) chloride, $CuCl_2$, (2.42 g, 18.0 mmol)

palladium(I) chloride, $PdCl_2$, (0.3192 g, 1.80 mmol)

anhydrous 1-butanol, (500 mL) and anhydrous acetonitrile (100 mL).

The reaction was conducted as in Example 1 except the reaction was carried out for 4 hours and the reaction vessel was initially pressurized to 52 bar gauge (750 psig) before air (130 psig) was added. The reaction was heated to ca. 80° C., which gave a final total pressure of 69 bar gauge (1000 psig). Approximately 83% of the product mixture (421.50 g) was charged to a medium-fritted filtration funnel. The dried product (16.57 g) containing the N-butoxy-carbonylamino-1,3,5-triazines, was obtained by removing both 1-butanol and acetonitrile from the filtrate under reduced pressure. A catalytic turnover number (TON) of 77 (mole butoxycarbonylamino groups/mole palladium) was determined from $^1$H-NMR. Product composition and total overall yield as determined by $^1$H-NMR was as follows: Tris-2,4,6-butoxycarbonylamino-1,3,5-triazine 75%, Bis-(2,4-butoxycarbonylamino)-6-amino-1,3,5-triazine 2.5%, mono-2-butoxycarbonylamino-4,6-diamino-1,3,5-triazine 0%.

Comparative Example C

Carbonylation of Melamine in the Presence of a Mixed Solvent System of 1-Butanol/Acetonitrile with a $Pd(II)Cl_2$/$CuCl_2$ Catalyst System Example 1 of European Patent Application 649,842 discloses a similar process except that stoichiometric amounts of copper (II) chloride and sodium phosphate dibasic is used, a 4:1 1-butanol/acetonitrile mixture is used, and the reaction temperature is 100° C. Further analysis of the product composition and total overall yield as determined by $^1$H-NMR was as follows: Tris-2,4,6-butoxycarbonylamino-1,3,5-triazine 1.4%, Bis-(2,4-butoxycarbonylamino)-6-amino-1,3,5-triazine 2%, mono-2-butoxycarbonylamino-4,6-diamino-1,3,5-triazine 14%.

Example 7

Carbonylation of Melamine in the Presence of 1-Butanol with 10% Pd on Carbon/$CuCl_2$ Catalyst System The process of Example 1 was repeated except that a catalytic quantity of Pd(0) on carbon was used.

A glass-lined, two-liter, 316 stainless steel ZIPPER-CLAVE® was charged with the following:

melamine (7.57 g, 60 mmol)

sodium phosphate, dibasic ($Na_2HPO_4$) (2.57 g, 18.1 mmol)

copper(II) chloride, $CUCl_2$, (2.42 g, 18.0 mmol)

10% Pd(0) on carbon, (3.19 g, 1.80 mmol) and anhydrous 1-butanol (600 mL).

The reaction was conducted as disclosed in Example 1 except that the reaction was allowed to react for approximately 16 hours. Approximately 38% of the product mixture (180.96 g) was charged to a medium-fritted filtration funnel containing CELITE® covered with a layer of silica gel. The dried product (5.82 g) containing the N-butoxycarbonylamino-1,3,5-triazines, was obtained by removing 1-butanol from the filtrate under reduced pressure. A catalytic turnover number (TON) of 59 (mole butoxycarbonylamino groups/mole palladium) was determined from $^1$H-NMR. Product composition and total overall yield as determined by ¹H-NMR was as follows: Tris-2,4,6-butoxycarbonylamino-1,3,5-triazine 55%, Bis-(2,4-butoxycarbonylamino)-6-amino-1,3,5-triazine 6%, mono-2-butoxycarbonylamino-4,6-diamino-1,3,5-triazine 0.3%.

Example 8

Carbonylation of Melamine in the Presence of 1-Butanol with an Intercalated $PdCl_2$ in Graphite/$CuCl_2$ Catalyst System The process of Example 1 was repeated except that a catalytic quantity of intercalated 3% $PdCl_2$ in graphite (GRAPHIMET™-$PdCl_2$-3) (at 0.5 mol % Pd on amino groups) was used.

A glass-lined, two-liter, 316 stainless steel ZIPPER-CLAVE® was charged with the following:

melamine (7.57 g, 60 mmol)

sodium phosphate, dibasic ($Na_2HPO_4$) (2.56 g, 18.0 mmol)

copper(II) chloride, $CuCl_2$, (2.42 g, 18.0 mmol)

3% $PdCl_2$ in Graphite (GRAPHIMET™-$PdCl_2$-3), (5.32 g, 0.90 mmol) and anhydrous 1-butanol (600 mL).

The reaction was conducted as in Example 1 except the reaction was carried out for 16 hours and the reaction vessel was initially pressurized to 52 bar gauge (750 psig) before air (130 psig) was added. The reaction was heated to ca. 80° C., which gave a final total pressure of 69 bar gauge (1000 psig). Approximately 97% of the product mixture (483.41 g) was charged to a medium-fritted filtration funnel. The dried product (13.80 g) containing the N-butoxy-carbonylamino-1,3,5-triazines, was obtained by removing 1-butanol from the filtrate under reduced pressure. A catalytic turnover number (TON) of 98 (mole butoxy-carbonylamino groups/mole palladium) was determined from ¹H-NMR. Product composition and total overall yield as determined by ¹H-NMR was as follows: Tris-2,4,6-butoxycarbonyl-amino-1,3,5-triazine 46%, Bis-(2,4-butoxycarbonylamino)-6-amino-1,3,5-triazine 5%, mono-2-butoxycarbonylamino-4,6-diamino-1,3,5-triazine 0.5%.

Example 9

Carbonylation of Melamine in the Presence of 1-Butanol with a $PdCl_2$/Intercalated $CuCl_2$ in Graphite Catalyst System The process of Example 1 was repeated except that intercalated 10% Cu(II)$Cl_2$ in graphite (Graphimet™-$CuCl_2$-10 was used (at 2.5 mol % Cu based on amino groups).

A glass-lined, two-liter, 316 stainless steel ZIPPER-CLAVE® was charged with the following:

melamine (7.57 g, 60 mmol)

sodium phosphate, dibasic ($Na_2HPO_4$) (0.85 g, 6.0 mmol)

10% copper(II) chloride in graphite, GRAPHIMET™-$CuCl_2$-10

(6.05 g, 4.50 mmol)

palladium(II) chloride, $PdCl_2$, (0.3192 g, 1.80 mmol) and anhydrous 1-butanol (600 mL).

The reaction was conducted as in Example 1 except the reaction was carried out for 4 hours and the reaction vessel was initially pressurized to 52 bar gauge (750 psig) before air (130 psig) was added. The reaction was heated to ca. 80° C., which gave a final total pressure of 69 bar gauge (1000 psig).

Approximately 80% of the product mixture (403.56 g) was charged to a medium-fritted filtration funnel. The dried product (4.2 g) containing the N-butoxycarbonylamino-1,3,5-triazines, was obtained by removing 1-butanol from the filtrate under reduced pressure. A catalytic turnover number (TON) of 19 (mole butoxy-carbonylamino groups/mole palladium) was determined from ¹H-NMR. Product composition and total overall yield as determined by ¹H-NMR was as follows: Tris-2,4,6-butoxycarbonylamino-1,3,5-triazine 17%, Bis-(2,4-butoxycarbonylamino)-6-amino-1,3,5-triazine 4%, mono-2-butoxycarbonylamino-4,6-diamino-1,3,5-triazine 0%.

Example 10

Carbonylation of Melamine in the Presence of 1-Butanol with a 0.1 mole % $PdCl_2$/10 mole % $CuCl_2$ Catalyst System The process of Example 1 was repeated except that a catalytic quantity of $PdCl_2$ (at 0.1 mol % Pd based on amino groups) was used with Cu(II)$Cl_2$ as co-catalyst (at 10 mol % Cu based on amino groups).

A glass-lined, two-liter, 316 stainless steel ZIPPER-CLAVE® was charged with the following:

melamine (7.57 g, 60 mmol)

sodium phosphate, dibasic ($Na_2HPO_4$) (2.56 g, 18.0 mmol)

copper(II) chloride, $CuCl_2$, (2.42 g, 18.0 mmol)

palladium(II) chloride, $PdCl_2$, (0.032 g, 0.18 mmol) and anhydrous 1-butanol (600 mL).

The reaction was conducted as in Example 1 except the reaction was carried out for 16 hours and the reaction vessel was initially pressurized to 52 bar gauge (750 psig) before air (130 psig) was added. The reaction was heated to ca. 80° C., which gave a final total pressure of 69 bar gauge (1000 psig).

Approximately 78% of the product mixture (380.1 g) was charged to a medium-fritted filtration funnel. The dried product (14.76 g) containing the N-butoxy-carbonylamino-1,3,5-triazines, was obtained by removing 1-butanol from the filtrate under reduced pressure. A catalytic turnover number (TON) of 677 (mole butoxy-carbonylamino groups/mole palladium) was determined from ¹H-NMR. Product composition and total overall yield as determined by ¹H-NMR was as follows: Tris-2,4,6-butoxycarbonylamino-1,3,5-triazine 63%, Bis-(2,4-butoxycarbonylamino)-6-amino-1,3,5-triazine 7%, mono-2-butoxycarbonylamino-4,6-diamino-1,3,5-triazine 0.5%.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. A method for preparing tris-carbamate triazine esters which comprises reacting a tris-(halo)amino-1,3,5-triazine compound in the presence of excess amounts of carbon monoxide and an alcohol, a sub-stoichiometric amount of a base, a catalyst system comprising a catalytic amount of a primary catalyst of a group VIII metal or metal salt, and a sub-stoichiometric amount of a co-catalyst of a group I-B or lanthanide series metal or metal salt, with the reaction being conducted at a temperature, pressure and length of time sufficient to form a tris-amino-1,3,5-carbamate ester in a yield of at least about 5 percent.

2. The method of claim 1, wherein the tris-carbamate triazine ester is tris-(butyl,methyl) carbamoyl triazine.

3. The method of claim 1, wherein the process forms a tris-carbamate triazine ester in a yield of at least about 10 percent and the triazine compound is a tris-(halo)amino-1,3,5-triazine compound of the formula:

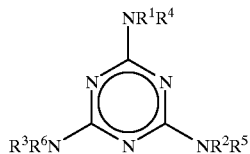

wherein $R^1$, $R^2$, and $R^3$ are the same or different and is hydrogen, halogen, hydroxy, hydrocarbyl, hydrocarbyloxy hydrocarbyl, nitroso, sulfanyl, aralkyl, or aryl whereby $R^1$, $R^2$, and $R^3$ are substituted or unsubstituted; and $R^4$, $R^5$, and $R^6$ are the same or different and are hydrogen or halogen.

4. The method of claim 3, wherein the process forms a tris-(halo)carbamate triazine ester in a yield of at least about 25% and $R^1$, $R^2$, and $R^3$ of the (halo)amino-1,3,5-triazine are each independently hydrogen, halogen, hydroxy, $C^1$ to $C^6$ alkyl, $C^3$ to $C^8$ cycloalkyl, $C^2$ to $C^6$ alkenyl, $C^2$ to $C^6$ alkynyl, or $C^1$ to $C^6$ alkoxy; and $R^4$, $R^5$, and $R^6$ are the same or different and are hydrogen or halogen.

5. The method of claim 4, wherein the (halo)amino-1,3,5-triazine compound is melamine.

6. The method of claim 1, wherein the primary catalyst comprises palladium, platinum, ruthenium, rhodium, or a mixture thereof.

7. The method of claim 6, wherein the primary catalyst comprises palladium (0), palladium (II) chloride, palladium (II) bromide, palladium (II) iodide, palladium (II) acetate, palladium (II) acetylacetonate, palladium (II) oxide, or a mixture thereof.

8. The method of claim 1, wherein the primary catalyst includes a catalytic support.

9. The method of claim 8, wherein the catalytic support is barium sulfate, carbon, calcium carbonate, silica, an aluminosilicate, a clay, a zeolite, a carbonaceous material, an intercalated material, a resin, a polymeric material, or a mixture thereof.

10. The method of claim 1, wherein the primary catalyst is present in an amount from about 0.05 mole percent to 10 mole percent.

11. The method of claim 1, wherein the co-catalyst comprises copper, cerium, or a mixture thereof.

12. The method of claim 11, wherein the cocatalyst comprises copper(II) chloride, copper(II) sulfate, cerium (III) stearate, or a mixture thereof.

13. The method of claim 1, wherein the co-catalyst is present in an amount from about 1 mole percent to 20 mole percent.

14. The method of claim 1, wherein the co-catalyst includes a catalytic support.

15. The method of claim 14, wherein the catalytic support is barium sulfate, carbon, calcium carbonate, silica, an aluminosilicate, a clay, a zeolite, a carbonaceous material, an inter calated material, a resin, a polymeric material, or a mixture thereof.

16. The method of claim 1, which further comprises regenerating the primary catalyst.

17. The method of claim 16, wherein the catalyst is regenerated with an oxidant system comprising molecular oxygen, an oxygen-containing gas, a metal-containing compound, or a mixture thereof.

18. The method of claim 17, wherein the metal-containing compound of the oxidant system is a group I-B metal, a lanthanide, or mixtures thereof.

19. The method of claim 1, wherein the alcohol is a straight or branched monohydric or polyhydric alkanol, straight or branched monohydric or polyhydric alkenol, monohydric or polyhydric cycloalkanol, monohydric or polyhydric arylalkanol, phenol, or a mixture thereof.

20. The method of claim 19, wherein the alcohol is a straight or branched $C_1$ to $C_{20}$ monohydric alcohol, a straight or branched $C_1$ to $C_{20}$ polyhydric alcohol, an alkanol of 1 to 20 carbons, or a mixture thereof.

21. The method of claim 20, wherein the alcohol is methanol, ethanol, 1-propanol, 2-propanol, 1-butanol, isobutanol, 2-methyl-2-propanol, 1-methoxy-2-propanol, 1-pentanol, 1-hexanol, 1-heptanol, 1-octanol, 2-ethyl-1-hexanol, or a mixture thereof.

22. The method of claim 20, wherein the alcohol is methanol, 1-butanol, or a mixture thereof.

23. The method of claim 1, wherein the reaction temperature is between about 40° C. to 150° C. and the base has a $pK_a$ of from about 4 to 13.

24. The method of claim 23, wherein the base is sodium phosphate dibasic, sodium phosphate, lithium phosphate, potassium phosphate, sodium pyrophosphate, potassium hydrogen phosphate, sodium acetate, potassium acetate, or a mixture thereof.

25. The method of claim 1, which further comprises conducting the reaction in the presence of a cosolvent or solvent mixture.

26. The method of claim 25, wherein the solvent is an alkyl nitrile, aryl nitrile, or a mixture thereof.

27. The method of claim 26, wherein the nitrile cosolvent is acetonitrile, propionitrile, butyronitrile, benzonitrile, or a mixture thereof.

28. The method of claim 26, wherein the nitrile solvent is acetonitrile.

29. The method of claim 1, wherein the carbon monoxide pressure is between about 450 psig to about 1050 psig.

30. The method of claim 1, wherein the reaction is conducted at a pressure from about 250 psig to about 1500 psig.

31. The method of claim 1, wherein an intermediate 1,3,5-triazine compound is formed prior to forming the tris-carbamate.

32. The method of claim 31, wherein the intermediate is an isocyanate.

* * * * *